United States Patent [19]

Aumueller et al.

[11] Patent Number: 4,943,391
[45] Date of Patent: Jul. 24, 1990

[54] BICYCLO(3.3.1)NONANE DERIVATIVES AND USE IN STABILIZING ORGANIC MATERIALS

[75] Inventors: Alexander Aumueller, Deidesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 286,295

[22] Filed: Dec. 10, 1988

[30] Foreign Application Priority Data

Dec. 29, 1987 [DE] Fed. Rep. of Germany ....... 3743279

[51] Int. Cl.$^5$ .................... C07D 471/08; C09K 15/18
[52] U.S. Cl. .................................. 252/401; 252/403; 544/354; 544/362; 546/122
[58] Field of Search ................ 546/122; 544/354, 362; 252/401, 403

[56] References Cited

U.S. PATENT DOCUMENTS 2,345,237 3/1944 Chitwood et al. ................... 544/350
4,769,457 9/1988 Helwig et al. ....................... 544/180

FOREIGN PATENT DOCUMENTS 272588 6/1988 European Pat. Off. .
272589 6/1988 European Pat. Off. .
272590 6/1988 European Pat. Off. .
272591 6/1988 European Pat. Off. .

OTHER PUBLICATIONS

Chemical Abstracts, vol. 56, 12900a to 12901e, (1962); Abstract of Chiavarelli et al.; Farmaco (Pavia) Ed. Sci. 16, pp. 313–325, (1961).

Primary Examiner—Richard A. Schwartz
Assistant Examiner—Bernard I. Dentz
Attorney, Agent, or Firm—Oblon, Spivak, McClelland, Maier & Neustadt

[57] ABSTRACT

Bicyclo[3.3.1]nonane derivatives of the general formula (I)

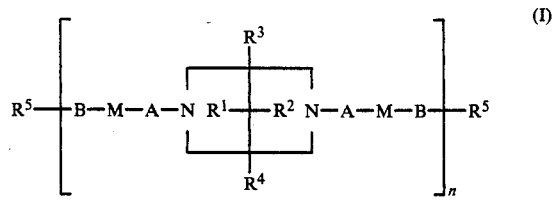

where
n is an integer from 1 to 70,
$R^1$ is hydrogen,
$R^2$ is hydrogen or hydroxyl, or the radical

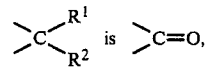 is $>C=O$, $R^3$ and $R^4$ are each independently of the other phenyl or 1- or 2-naphthyl, which phenyl or naphthyl may each be substituted by 1, 2 or 3 $C_1$–$C_{12}$-alkyls, $C_1$–$C_{12}$-alkoxys, chlorines, bromines, fluorines, trifluoromethyls or cyanos, in the case of 2 or 3 substituents these substituents being identical or different,
A and B are each independently of the other a chemical bond, $C_1$–$C_{22}$-alkylene, cycloalkylene

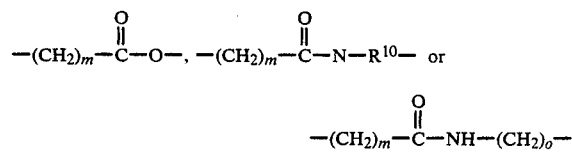

where
m and o are each from 1 to 20 and
$R^{10}$ is hydrogen, $C_1$–$C_{22}$-alkyl, $C_5$–$C_{12}$-cycloalkyl, $C_7$–$C_{18}$-phenylalkyl, phenyl or $C_2$–$C_{22}$-cyanoalkyl,
M is a radical of the formula

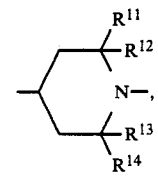

which may be bonded to A not only via the nitrogen atom but also via the carbon atom, and
$R^{11}$, $R^{12}$, $R^{13}$ and $R^{14}$ are each independently of the others $C_1$–$C_4$-alkyl, or
$R^{11}$ and $R^{12}$ and/or $R^{13}$ and $R^{14}$ are each together tetramethylene or pentamethylene,
$R^5$ is hydrogen, cyano, hydroxyl,

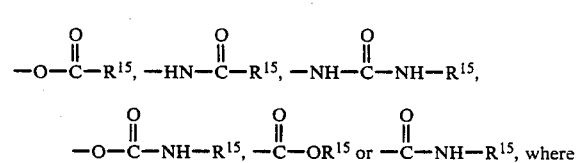

$R^{15}$ is hydrogen, $C_1$–$C_{22}$-alkyl, $C_5$–$C_{12}$-cycloalkyl, $C_5$–$C_{16}$-phenylalkyl or a 5- or 6-membered heterocycle, or, when n is 1, —M—B—$R^5$ is a radical of the formula (Abstract continued on next page.)

-continued
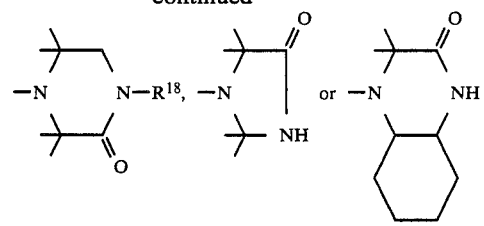
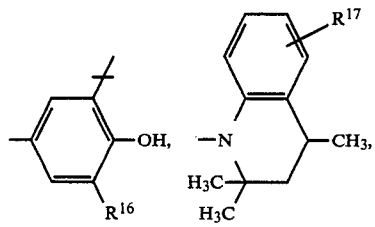
where
R$^{16}$ is C$_1$–C$_4$-alkyl,
R$_{17}$ is hydrogen, C$_1$–C$_4$-alkyl or C$_1$–C$_4$-alkoxy and
R$_{18}$ is hydrogen or C$_1$–C$_{12}$-alkyl, have remarkably good stabilizing properties in respect of plastics, are colorless, are highly compatible with organic polymers and are stable to thermal decomposition.
13 Claims, No Drawings

BICYCLO(3.3.1)NONANE DERIVATIVES AND USE IN STABILIZING ORGANIC MATERIALS

It is known that polyalkylpiperidine derivatives and sterically hindered phenols protect organic polymers from destruction by light and heat.

Unsatisfactory aspects of prior art compounds frequently include the low compatibility with polyolefins and other plastics, the duration of the protective effect, the self-color of the substances, the tendency toward volatility and the thermal decomposition of the stabilizers in the course of incorporation at elevated temperature.

It is an object of the invention to provide novel stabilizers which do not have the foregoing disadvantages.

We have found that this object is achieved with the novel heterocycles of the formula (I). Accordingly, the present invention provides bicyclo[3.3.1]nonane derivatives of the general formula (I)

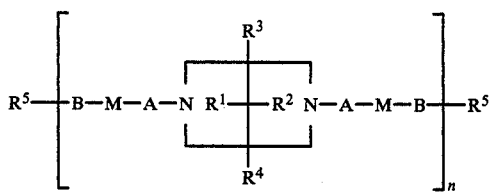

where
n is an integer from 1 to 70,
$R^1$ is hydrogen,
$R^2$ is hydrogen or hydroxyl, or the radical

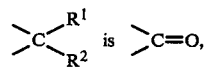

$R^3$ and $R^4$ are each independently of the other phenyl or 1- or 2-naphthyl, which phenyl or naphthyl may each be substituted by 1, 2 or 3 $C_1$-$C_{12}$-alkyls, $C_1$-$C_{12}$-alkoxys, chlorines, bromines, fluorines, trifluoromethyls or cyanos, in the case of 2 or 3 substituents these substituents being identical or different, A and B are each independently of the other a chemical bond, $C_1$-$C_{22}$-alkylene, cycloalkylene

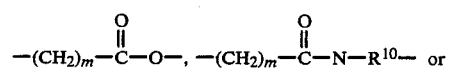

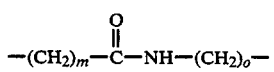

where
m and o are each from 1 to 20 and
$R^{10}$ is hydrogen, $C_1$-$C_{22}$-alkyl, $C_5$-$C_{12}$-cycloalkyl, $C_7$-$C_{18}$-phenylalkyl, phenyl or $C_2$-$C_{22}$-cyanoalkyl,
M is a radical of the formula

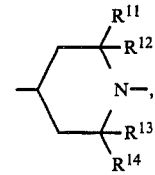

which may be bonded to A not only via the nitrogen atom but also via the carbon atom, and
$R^{11}$, $R^{12}$, $R^{13}$ and $R^{14}$ are each independently of the others $C_1$-$C_4$-alkyl, or
$R^{11}$ and $R^{12}$ and/or $R^{13}$ and $R^{14}$ are each together tetramethylene or pentamethylene,
$R^5$ is hydrogen, cyano, hydroxyl,

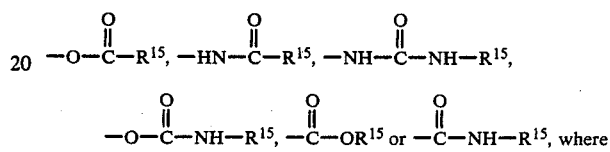

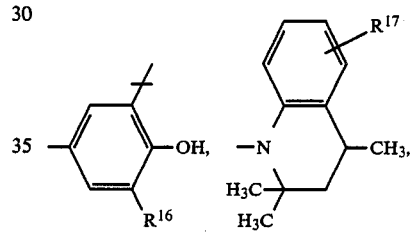

$R^{15}$ is hydrogen, $C_1$-$C_{22}$-alkyl, $C_5$-$C_{12}$-cycloalkyl, $C_5$-$C_{16}$-phenylalkyl or a 5- or 6-membered heterocycle, or, when n is 1, —M—B—$R^5$ is a radical of the formula

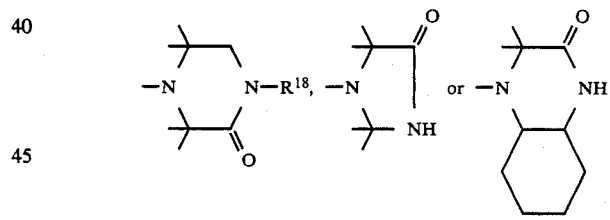

where $R^{16}$ is $C_1$-$C_4$-alkyl,
$R_{17}$ is hydrogen, $C_1$-$C_4$-alkyl or $C_1$-$C_4$-alkoxy and
$R_{18}$ is hydrogen or $C_1$-$C_{12}$-alkyl.

The compounds according to the invention have a very good stabilizing effect on plastics. They have no self-color, they are highly compatible with organic polymers, they have a low vapor pressure, and they are stable to thermal decomposition.

The compounds according to the invention are therefore highly suitable for stabilizing organic material, in particular plastics, against degradation by light and heat. They are also effective metal deactivators.

Preference is given to compounds (I) where n is an integer from 1 to 10. Particular preference is given to compounds (I) where n=1.

$R^{11}$, $R^{12}$, $R^{13}$ and $R^{14}$ are each preferably methyl.

The alkyl radicals $R^{10}$, $R^{15}$, $R^{16}$, $R^{17}$ and $R^{18}$ may be linear or branched. Specific examples of these alkyl radicals are: methyl, ethyl, propyl, isopropyl, butyl, isobutyl, pentyl, hexyl, i-octyl, octyl, nonyl, decyl, lauryl, stearyl and palmityl.

Cycloalkyl for $R^{10}$ and $R^{15}$ is for example cyclopentyl, cyclohexyl, cycloheptyl, cyclooctyl or cyclododecyl.

$R^2$ is preferably hydroxyl.

Preference is further given to compounds of the general formula (I) where the radical

is carbonyl.

$R^{15}$ is preferably $C_1$–$C_6$-alkyl, for example ethyl, propyl, isopropyl, butyl, isobutyl, pentyl or n- or i-hexyl. $R^{18}$ is preferably hydrogen or methyl and in particular tertiary butyl.

Heterocyclyl $R^5$ is derived for example from thiophene, furan, pyridine or a methyl derivative thereof.

Phenylalkyl for $R^{10}$ and $R^{15}$ is for example benzyl, methylbenzyl, 2-phenylethyl, 2- or 3phenylpropyl or 2-, 3- or 4-phenylbutyl.

Suitable alkylene for A and B is $C_1$–$C_{22}$-alkylene, preferably $C_1$–$C_6$-alkylene, the alkylene being linear or branched.

A and B can each also be a radical of the formula —(CH$_2$)$_m$—CO—N(R$^{10}$)—(CH$_2$)$_m$—CO—O and —(CH$_2$)$_m$—CO—NH—(CH$_2$)$_o$, where m is from 1 to 20, preferably from 1 to 3, o is 1 to 20, preferably from 1 to 6, in particular from 1 to 3, and $R^{10}$ is hydrogen, methyl or ethyl.

A and B are each particularly preferably —CH$_2$— and —CH$_2$—CH$_2$— and very particularly preferably a direct bond.

Particular preference is given to those compounds of the formula I where A—M—B—$R^5$ is 2,2,6,6-tetramethylpiperidin-4-yl or 1,2,2,6,6-pentamethyl-piperidin-4-yl.

Preferable $R^3$ and $R^4$ are phenyl and 1- or 2-naphthyl, which phenyl or naphthyl may carry 1, 2 or 3 substituents. Suitable substituents are: $C_1$–$C_{12}$-alkyl, $C_1$–$C_{12}$-alkoxy, chlorine, bromine, fluorine, trifluoromethyl and cyano, in the case of 2 or 3 substituents being present these substituents being identical or different.

Preferably, $R^3$ and $R^4$ are each phenyl which may be substituted once or twice. Specific examples of radicals for $R^3$ and $R^4$ are: phenyl, 2-, 3- or 4-tolyl, 3- or 4-methoxyphenyl, 3- or 4-ethoxyphenyl, 3- or 4-chlorophenyl, 3- or 4-bromophenyl, 3- or 4-fluorophenyl, 3,4-dimethylphenyl, 3- or 4-trifluoromethylphenyl, 4-tert-butylphenyl, 4-n-butoxyphenyl, 4-hexoxyphenyl, 4-dodecyloxyphenyl and 3,4-dimethoxphenyl. Unsubstituted phenyl is particularly preferred.

Of very particular importance is the bicyclo-[3.3.1]nonane derivative of the formula

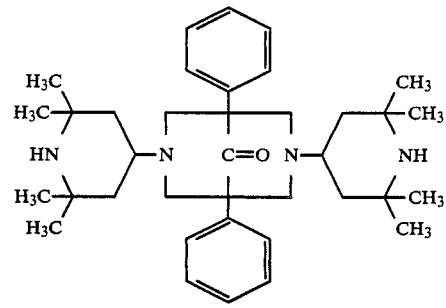

Compounds of the general formula (I) where

is carbonyl can be prepared in a conventional manner by reacting compounds of the general formula (II) with at least 4 equivalents of formaldehyde or of a formaldehyde-forming compound and at least 2 equivalents of a primary amine of the general formulae (III) to (IX)

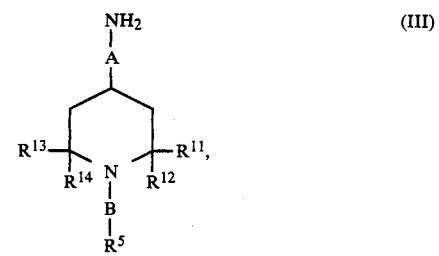

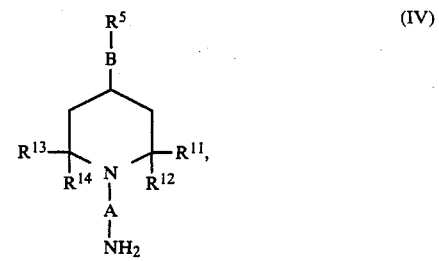

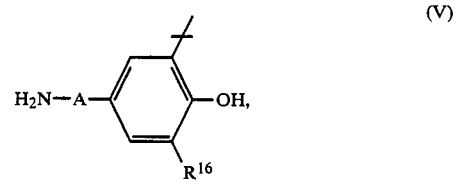

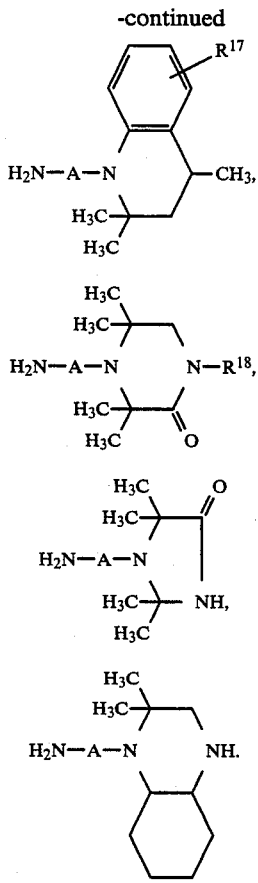

The preparation of similar bicyclo[3.3.1]nonane derivatives is described for example in J. Chem. Soc. 1951, 1706.

Preferably, the reaction is carried out in a solvent. Preferred solvents are water and alcohols, in particular methanol and ethanol.

In those cases where

is carbonyl, it may be converted by means of reducing agents such as hydrogen or metal hydrides, for example lithium aluminum hydride and in particular sodium borohydride, into a —CHOH group.

The compounds (I) according to the invention can be present in the form of free bases, as hydrates or as salts. Suitable anions come for example from inorganic acids, carboxylic acids and sulfonic acids. Of the salts, those of carboxylic acids and sulfonic acids are preferred.

Suitable inorganic anions are for example chloride, bromide, sulfate, methosulfate, tetrafluoroborate, phosphate and thiocyanate.

Carboxylic acid anions are for example: formate, acetate, propionate, hexanoate, cyclohexanoate, lactate, stearate, palmitate, dodecylbenzoate, benzoate, acrylate, methacrylate, citrate, malonate and succinate and also anions of polycarboxylic acids, such as polyacrylic acid, polymethacrylic acid and (meth)acrylic acid copolymers having up to 3,000 COOH groups.

Sulfonic acid anions are for example benzenesulfonate, tosylate and methanesulfonate.

The compounds (I) are added to the plastics to be stabilized in a concentration of from 0.01 to 5% by weight, preferably of 0.02 to 2% by weight, before, during or after polymer formation.

To prepare a mixture of a compound according to the invention and a plastic to be stabilized it is possible to use any existing process for mixing stabilizers or other additives into polymers.

In addition to a compound (I) according to the invention, the stabilized plastics may also contain further additives, for example antioxidants, additional light stabilizers, metal deactivators, antistats, flame retardants and also pigments and fillers.

Antioxidants and light stabilizers which may be added to plastics in addition to compounds (I) of the invention are for example compounds based on sterically hindered phenols of sulfur- and/or phosphorus-containing costabilizers.

Examples of such phenolic antioxidants are 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-tri-methyl-2,4,5-tris-(3,5-di-tert-butyl-4-hydroxybenzyl)benzene, 1,3,5-tris-(3,5-di-tert-butyl-4-hydroxybenzyl) isocyanurate, 1,3,5-tris[β-(3,5-di-tert-butyl-4-hydroxyphenyl)-propionyloxyethyl] isocyanurate, 1,3,5-tris-(2,6-dimethyl-3-hydroxy-4-tert-butylbenzyl) isocyanurate and pentaerythritol tetrakis[β-(3,5-di-tert-butyl-4-hydroxyphenyl)propionate].

Phosphorus-containing antioxidants are for example tris(nonylphenyl) phosphite, distearyl pentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl) 4,4'-diphenylene diphosphite.

Sulfur-containing antioxidants are for example dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Further antioxidants and light stabilizers which may be used together with the compounds according to the invention are for example 2-(2'-hydroxyphenyl)benzotriazoles, 2-hydroxybenzophenones, phenyl esters of hydroxybenzoic acids, α-cyanocinnamic acid derivatives, nickel compounds and/or oxalic dianilides.

Examples of organic polymers which may be stabilized with compounds according to the invention are:

polymers of mono- and diolefins, such as polyethylene of low of high density, linear polyethylene of low density, propylene, polyisobutylene, polybutene-1, polyisoprene or polybutadiene, and also copolymers of mono- or diolefins and mixtures thereof;

copolymers of mono- or diolefins with further vinyl monomers, for example ethylene/alkyl acrylate copolymers, ethylene/alkyl methacrylate copolymers, ethylene/vinyl acetate copolymers or ethylene/acrylic acid copolymers; polystyrene; copolymers of styrene or α-methylstyrene and dienes or acrylic derivatives, such as styrene/butadiene, styrene/acrylonitrile, styrene-/ethyl methacrylate, styrene/butadiene/ethyl acrylate, styrene/acrylonitrile/methacrylate; ABS, MBS or similar polymers; halogen-containing polymers, for example polyvinyl chloride, polyvinyl fluoride, polyvinylidene fluoride and copolymers thereof; polymers which derive from α,β-unsaturated acids and derivatives thereof, such as polyacrylates and polymethacrylates, polyacrylamides and polyacrylonitriles; polymers which derive from unsaturated alcohols and amines or from acrylic derivatives or acetals thereof, such as polyvinyl alcohol or polyvinyl acetate; polyurethanes, polyamides, polyureas, polyesters, polycarbonates, polysulfones, polyether sulfones and polyether ketones.

Further organic polymers which may be stabilized with the compounds according to the invention are industrial coatings. Of these, baking finishes, of which in turn automotive finishes, preferably two-coat finishes, must be mentioned in particular. Here too it is possible to add the aforementioned further antioxidants and light stabilizers.

The compounds according to the invention may be added to the coating composition in solid or dissolved form. The high solubility of (I) in coating systems is of particular advantage here.

The compounds according to the invention are suitable in particular for stabilizing polyolefins, in particular ethylene and propylene polymers, polyurethanes and coating materials.

The invention is illustrated by the Examples below.

In no case are the reported yields optimized yields.

EXAMPLE 1

15 g of 1,3-diphenylacetone, 468 g of 2,2,6,6-tetramethyl-4-aminopiperidine and 225 g of paraformaldehyde were boiled in 1.2 l of ethanol for 6 hours. After cooling down, the precipitate was filtered off with suction, washed with a little ethanol and dried. 563 g were isolated of compound of the formula

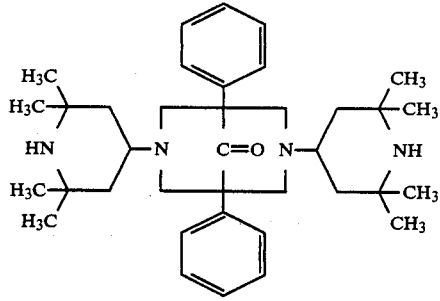

in the form of a colorless solid having a melting point of 212°–213° C.

EXAMPLE 2

14.3 g of product of Example 1 were dissolved in a little methanol and admixed with 1 g of sodium borohydride. The mixture was heated at 50° C. for 2 hours and cooled down, and the precipitated solid was filtered off with suction, washed with water and dried. 9.7 g were isolated of the compound of the formula

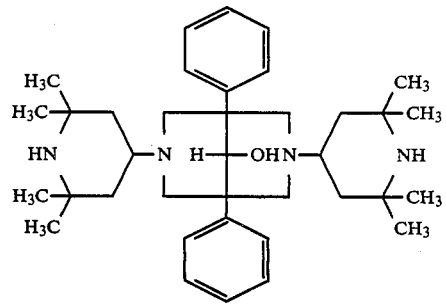

in the form of a colorless solid having a melting point of 254°–259° C.

EXAMPLE 3

To 28.6 g of the product of Example 1 were added with ice cooling a mixture of 80 ml of 98% strength formic acid and 15 ml of water and 6 g of a 30% strength aqueous formaldehyde solution. The mixture was heated at 95° C. for 6 hours and then cooled down, 10 ml of concentrated hydrochloric acid were added, and the mixture was concentrated and made alkaline with 25% strength aqueous sodium hydroxide solution. The water was decanted off the precipitated product. The product was recrystallized from a little ethanol. 10.3 g were isolated of the compound of the formula

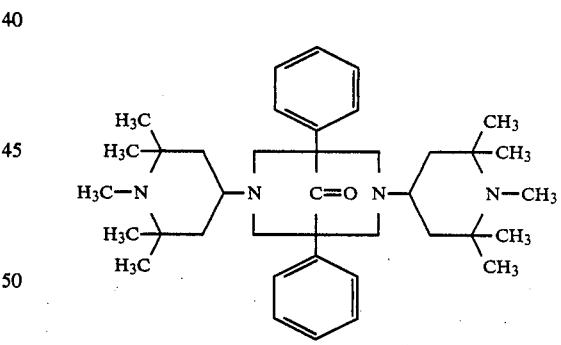

in the form of a colorless solid having a melting point of 170°–173° C.

EXAMPLE 4

To 9.4 g of the product of Example 3 in 250 ml of methanol were added 1.75 g of sodium borohydride, and the mixture was heated at 50° C. for 4.5 hours. It was then filtered, the filter residue was added to 500 ml of water, and the resulting precipitate was filtered with suction (6.0 g). Recrystallization from acetonitrile gave 3.15 g of the compound of the formula

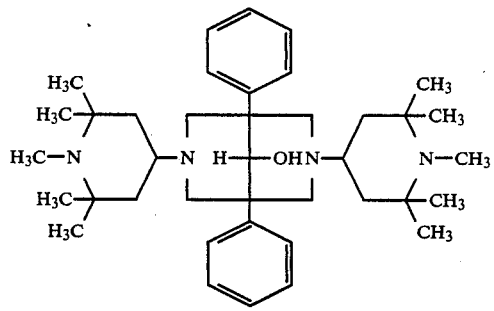

in the form of a colorless solid having a melting point of 239°–242° C.

EXAMPLE 5

12.5 ml of ethanol saturated with potassium carbonate, 15 g of paraformaldehyde, 1.2 g of potassium carbonate and 42.5 g of acetonecyanohydrin were maintained at from 25 to 30° C. for 2 hours and then brought to pH 6 from 85% strength phosphoric acid. 400 ml of ethanol and 71.5 g of the product of Example 1 were added, and the mixture was maintained at the boil for hours. After cooling down, the precipitate was filtered off with suction, heated with 500 ml of water at 80° C., filtered off hot with suction and dried. This gave 72 g of the compound of the formula

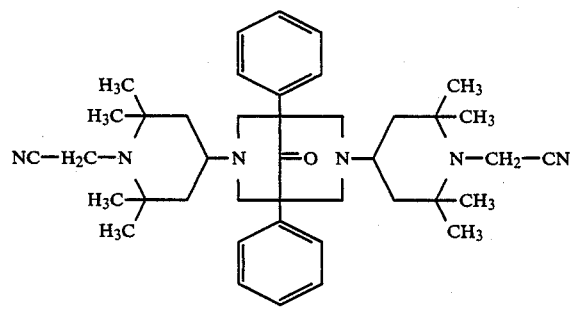

in the form of the semihydrate of melting point 230°–233° C.

EXAMPLE 6

11.9 g of 1,3-di(4'-methylphenyl)acetone, 15.6 g of 2,2,6,6-tetramethyl-4-aminopiperidine and 7.5 g of paraformaldehyde were refluxed in 40 ml of ethanol for 16 hours. The clear solution was reduced to about 75% of its volume in a rotary evaporator. The concentrate was cooled in an ice bath, and the resulting precipitate was filtered off with suction and washed with a little methanol. 14.4 g were isolated of the compound of the formula

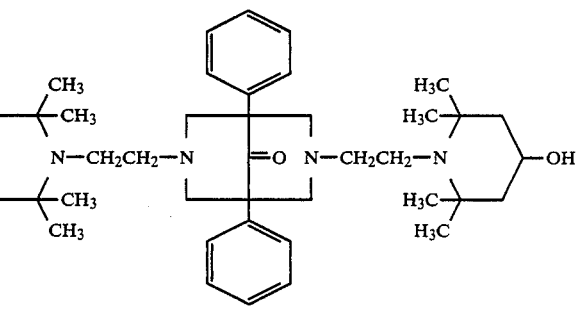

in the form of a colorless solid having a melting point of 110°–113° C. The substance contains 0.25 mol of water.

EXAMPLE 7

38 g of 1-β-aminoethyl-2,2,6,6-tetramethyl-4hydroxypiperidine (DE-A No. 3,208,570), 14.7 g of 1,3diphenylacetone and 9 g of paraformaldehyde were boiled in 150 ml of ethanol for 18.5 hours. After cooling down, the reaction solution was slowly added dropwise with stirring to 2 l of water at room temperature. The resulting precipitate was filtered off with suction, washed with water and dried in air. After boiling out with n-heptane, the residue was recrystallized from toluene in the presence of active charcoal. 22 g were obtained of the compound of the formula in the form of a colorless solid having a melting point of 193° C.

EXAMPLE 8

(a) 400 ml of ethanol, 678 g of ethyl cyanoacetate and 930 g of 2,2,6,6-tetramethyl-4-aminopiperidine were boiled for 7 hours and then cooled down to 10° C. in an ice bath. The resulting precipitate was filtered off with suction and washed with cold ethyl acetate. This gave 680 g of the compound of the formula

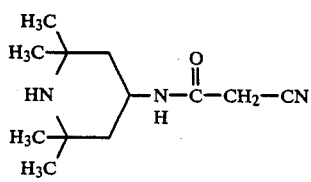

in the form of a colorless solid having a melting point of 148° C.

(b) 112 g of the product of Example 8(a) were hydrogenated in the presence of 25 g of Raney nickel and 100 g of ammonium in 1,000 ml of toluene at 90° C. under a hydrogen pressure of 200 bar until the pressure was constant. After the catalyst had been filtered off, the filtrate was concentrated, and the concentrate was distilled in the presence of a high-boiling propylene oxide/ethylene oxide block polymer having an average molecular weight of about 6,000 (Pluriol ® PE 6400 from BASF). This gave 80 g of the compound of the formula

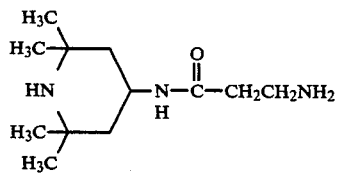

in the form of a colorless oil having a boiling point of 155° C./0.4 mm Hg, which solidified on standing.

(c) 33 g of the product of Example 8(b), 13.6 g of 1,3-diphenylacetone and 7.8 g of paraformaldehyde were boiled in 150 ml of ethanol for 20 hours. The solvent was then distilled off in a water jet vacuum, the tacky residue was dissolved in a mixture of 200 g of water and 10 g of concentrated sulfuric acid, and the solution was extracted with 200 ml of ethyl acetate. The aqueous phase was admixed with a little active charcoal, filtered and made alkaline with concentrated sodium hydroxide solution. The resulting precipitate was filtered off with suction, dried in air and recrystallized from a mixture of methylcyclohexane and toluene to give 13.9 g of a compound of the formula

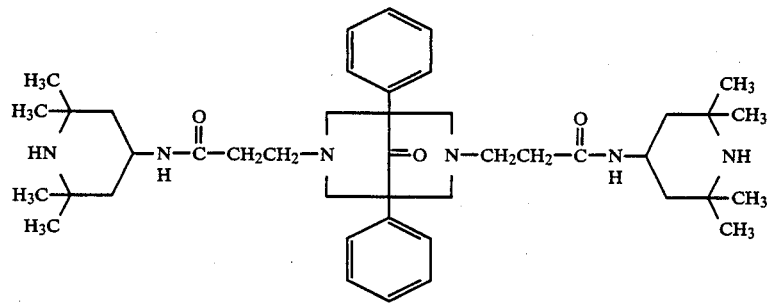

having a melting point of 88° C.

We claim:

1. A heterocyclic bicyclo[3.3.1]nonane derivative of the formula (I)

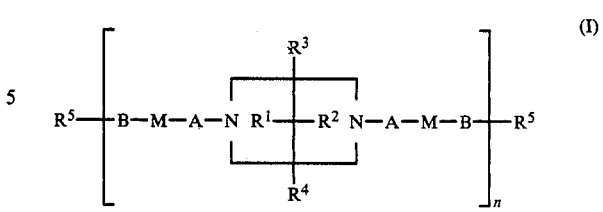

where
n is 1,
$R^1$ is hydrogen,
$R^2$ is hydrogen or hydroxyl, or the radical

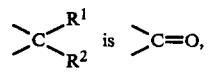 is $>C=O$, $R^3$ and $R^4$ are each independently of the other phenyl or 1- or 2-naphthyl, which phenyl or naphthyl may each be substituted by 1, 2 or 3 $C_1$–$C_{12}$-alkyls, $C_1$–$C_{12}$-alkoxys, chlorines, bromines, fluorines, trifluoromethyls or cyanos, in the case of 2 or 3 substituents these substituents being identical or different, A and B are each independently of the other a chemical bond, $C_1$–$C_{22}$-alkylene, cycloalkylene

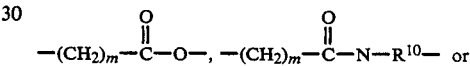

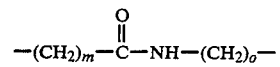

where
m and o are each from 1 to 20 and
$R^{10}$ is hydrogen, $C_1$–$C_{22}$-alkyl, $C_5$–$C_{12}$-cycloalkyl, $C_7$–$C_{18}$-phenylalkyl, phenyl or $C_2$–$C_{22}$-cyanoalkyl, M is a radical of the formula

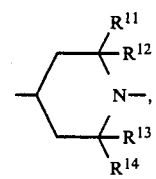

which may be bonded to A not only via the nitrogen atom but also via the carbon atom, and $R^{11}$, $R^{12}$, $R^{13}$ and $R^{14}$ are each independently of the others $C_1$-$C_4$-alkyl, or $R^{11}$ and $R^{12}$, $R^{13}$ and $R^{14}$ or $R^{11}$ and $R^{12}$ as well as $R^{13}$ and $R^{14}$ are each together tetramethylene or pentamethylene, $R^5$ is hydrogen, cyano, hydroxyl,

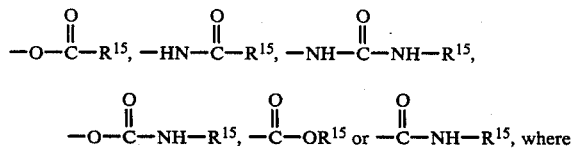

, where $R^{15}$ is hydrogen, $C_1$-$C_{22}$-alkyl, $C_5$-$C_{12}$-cycloalkyl, $C_5$-$C_{16}$-phenylalkyl or a 5- or 6-membered heterocycle, or —M—B—$R^5$ is a radical of the formula

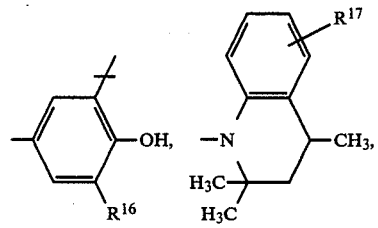

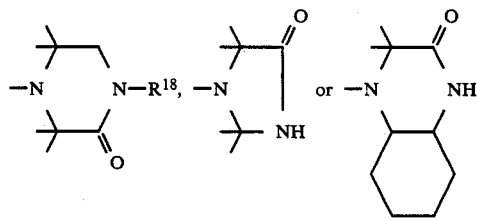

where $R^{16}$ is $C_1$-$C_4$-alkyl, $R^{17}$ is hydrogen, $C_1$-$C_4$-alkyl or $C_1$-$C_4$-alkoxy and $R^{18}$ is hydrogen or $C_1$-$C_{12}$-alkyl.

2. A bicyclononane derivative as claimed in claim 1, wherein $R^{11}$, $R^{12}$, $R^{13}$ and $R^{14}$ are each methyl.

3. A bicyclononane derivative as claimed in claim 2, wherein $R^2$ is hydroxyl or the radical $$\mathrm{>C<^{R^1}_{R^2}}$$

is carbonyl.

4. A bicyclononane derivative as claimed in claim 1, wherein $R^3$ and $R^4$ are each phenyl.

5. A bicyclononane derivative as claimed in claim 2, wherein $R^3$ and $R^4$ are each phenyl.

6. A bicyclononane derivative as claimed in claim 8, wherein $R^3$ and $R^4$ are each phenyl.

7. A bicyclononane derivative as claimed in claim 1, wherein A and B are each a direct bond.

8. A bicyclononane derivative as claimed in claim 3, wherein A and B are each a direct bond.

9. A bicyclononane derivative as claimed in claim 1, wherein A is —CH$_2$—CH$_2$—.

10. A bicyclononane derivative as claimed in claim 7, wherein A is —CH$_2$—CH$_2$—.

11. A bicyclononane derivative as claimed in claim 1, wherein A—M—B—$R^5$ is 2,2,6,6-tetramethylpiperidin-4-yl or 1,2,2,6,6-pentamethylpiperidin-4-yl.

12. A bicyclononane derivative as claimed in claim 3, wherein A—M—B—$R^5$ is 2,2,6,6-tetramethylpiperidin-4-yl or 1,2,2,6,6-pentamethylpiperidin-4-yl.

13. A stabilized organic material containing a bicyclononane derivative as claimed in claim 1 in which said derivative acts as a stabilizer.

* * * * *

UNITED STATES PATENT AND TRADEMARK OFFICE
CERTIFICATE OF CORRECTION

PATENT NO. : 4,943,391

DATED : JULY 24, 1990

INVENTOR(S) : ALEXANDER AUMELLER ET AL.

It is certified that error appears in the above-identified patent and that said Letters Patent is hereby corrected as shown below:

ON THE TITLE PAGE

Item [22] Filed: "December 10, 1988" should read --December 19, 1988--.

Item [30] Foreign Application Priority Data: "December 29, 1987" should read --December 19, 1987--.

Signed and Sealed this

Seventeenth Day of March, 1992

Attest:

HARRY F. MANBECK, JR.

*Attesting Officer*     *Commissioner of Patents and Trademarks*